United States Patent [19]

Anderson et al.

[11] Patent Number: 4,858,154

[45] Date of Patent: Aug. 15, 1989

[54] INTERLABORATORY QUALITY ASSURANCE PROGRAM

[75] Inventors: Frank C. Anderson, Hialeah; Dean E. Twedt, Miami, both of Fla.

[73] Assignee: Coulter Electronics, Inc., Hialeah, Fla.

[21] Appl. No.: 848,887

[22] Filed: Apr. 7, 1986

[51] Int. Cl.[4] .............................................. G01N 15/02
[52] U.S. Cl. ................................. 364/554; 364/552; 364/551.01
[58] Field of Search ............... 364/551, 552, 554, 555, 364/739, 416

[56] References Cited

U.S. PATENT DOCUMENTS

| | | | |
|---|---|---|---|
| 2,398,988 | 4/1946 | Ziebolz | 364/554 |
| 3,151,237 | 9/1964 | Hrabak | 235/151 |
| 3,549,994 | 12/1970 | Rothermel et al. | 324/71 |
| 4,202,033 | 5/1980 | Strobel | 364/571 |
| 4,299,726 | 11/1981 | Crews et al. | 252/408 |
| 4,320,463 | 3/1982 | Himmelstein | 364/552 |
| 4,405,719 | 9/1983 | Crews et al. | 436/10 |
| 4,596,464 | 6/1986 | Hoffman et al. | 356/36 |

OTHER PUBLICATIONS

Kampen et al., "Quality Control and Hematology 1975".
Gilmor et al., "Calibration Methods for Automated Hermatology Instruments, 7/1977".
Koepke, "The Calibration of Automated Instruments for Accuracy in Hemoglobinometry", 7/77.
Bull, "A Statistical Approach to Quality Control", 1975.
Theodore Colton, Sc.D., "Statistics in Medicine", (1974) pp. 36–39.
John M. England, "Medical Research", (1975) Chapter 1, pp. 1–8.
Peachy R. Gilmer, Jr. et al., "The Status of Methods of Calibration in Hematology", Am. Soc. Clin. Path., vol. 74, No. 4, Supplement (1980) pp. 600–605.

Primary Examiner—Parshotam S. Lall
Assistant Examiner—Ellis B. Ramirez
Attorney, Agent, or Firm—Gerald R. Hibnick; Allen B. Curtis

[57] ABSTRACT

An improved procedure for statistically evaluating the performance, precision and/or accuracy, of at least one analytical instrument in a pool of like or substantially like instruments by comparing the performance of the one instrument located in one laboratory with the performance of like instruments in other laboratories. The procedure includes the step of quantitatively analyzing a reference or control specimen of known constituents by each instrument in the pool and collecting the resultant data from the one instrument in the pool and of the pool instruments. The mean data from the one instrument and of the pool instruments are mathematically correlated in a series of statistical equations for computing a novel, sensitive index known as the "Instrument Performance Index" or IPI. This IPI can be tabulated and/or graphically displayed, preferably as a single point in a Cartesian coordinate system, whereby an operator can tell at a glance the performance level with respect to both precision and accuracy of the one instrument in the pool. The ultimate IPI is composed of a novel Coefficient of Variation Index (CVI), which is a valuable measure of instrument precision, and the Standard Deviation Index (SDI), which is a measure of performance accuracy. Both the CVI and SDI are derived values according to the invention and are capable of tabulation and display.

15 Claims, 2 Drawing Sheets

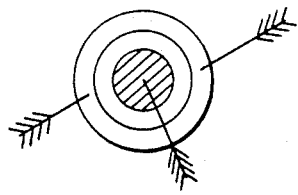
FIG_1A.
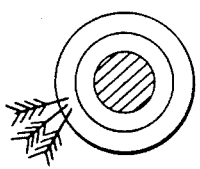
FIG_1B.
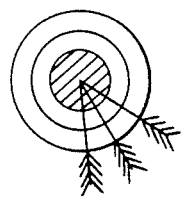
FIG_1C.
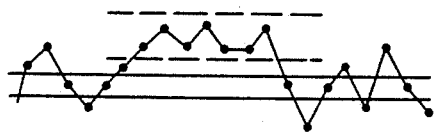
FIG_2A.
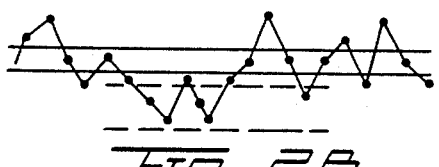
FIG_2B.
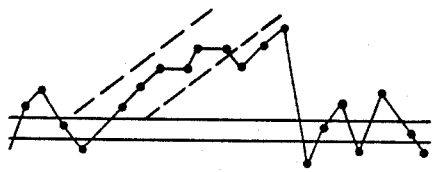
FIG_2C.
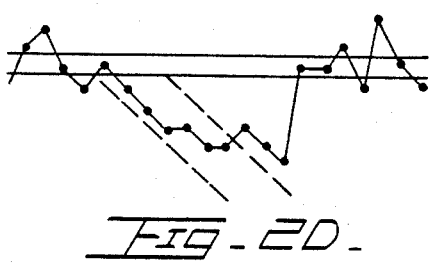
FIG_2D.
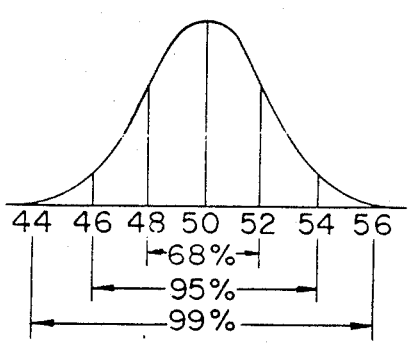
FIG_3.
PARTICIPANT PRH 205
| WBC | | | | | | | |
|---|---|---|---|---|---|---|---|
| | | | | ● | | | 3CVI |
| | | | | | | | 2CVI |
| | | | | | | | 1CVI |
−3SDI  −2SDI  −1SDI  +1SDI  +2SDI  +3SDI
MEAN
RBC — dot near mean (+1SDI area)
Hgb — dot at −3SDI
Hct — dot at +3SDI
MCV — dot at −2SDI
PLT — dot near mean
MPV — dot near −1SDI
CELL CONTROL LOT NUMBER 443
FIG_4.

INTERLABORATORY QUALITY ASSURANCE PROGRAM

BACKGROUND OF THE INVENTION

1. Field of the Invention

This invention relates to an improved procedure for evaluating the performance of at least one apparatus in a pool of like apparatuses. Such performance evaluation lies within the category of quality assurance or QA and quality control or qc. In the field of biomedical and laboratory equipment and apparatus, the QA can be accomplished by comparing the performance of a specific type of equipment or apparatus, located in one laboratory, with the performance of like apparatuses in other laboratories, often in other cities and states. Such an evaluation program is called an Interlaboratory Quality Assurance Program-IQAP.

The field of this invention is directed to statistical comparisons of apparatus performance. Accordingly, to set forth the invention in a meaningful environment and best mode, a specific type of laboratory apparatus needs to be identified. One such apparatus is a blood analyzer sold by Coulter Electronics, Inc. under the trademark COULTER COUNTER ® and is exemplified by U.S. Pat. No. 3,549,994. Such an apparatus was called the Model S and has been modified and improved over the past seventeen years to become two full series of semi-automatic hematology analyzers, well known throughout the world.

The need for a highly informative and readily usable IQAP for laboratory equipment, especially hematology analyzers, is self-evident. These apparatuses are complex and provide quantitative data on numerous blood parameters, for example: the red blood cell counter (RBC), hematocrit (Hct), hemoglobin (Hgb), mean corpuscular volume (MCV), mean corpuscular hemoglobin (MCH), the mean corpuscular hemoglobin concentration (MCHC), and the white blood cell count (WBC). Definitions of each of these parameters are set forth in U.S. Pat. No. 3,549,994. Quantitative data also can be obtained from other components of the blood, for example, platelets, neutrophils, eosinophils, lymphocytes, and monocytes, by use of current generation COULTER COUNTER analyzers.

Quality control for hematology equipment is a relatively complex issue for two essential reasons, the first being the lack of standards, i.e. materials with a known number of analytical variables; and the second being the number of analytical variables that can affect test result performance. Other significant factors affecting the relative accuracy of test results can be (1) changes in calibration, (2) specimen stability or shelf life, (3) reagent condition, and (4) instrument performance.

Many hematology apparatus quality control techniques have been utilized in the laboratory and are in use today. They are: calibration, commercial controls, XB analysis (called "X bar B"), interlaboratory comparison, and technologist review.

Calibration is a method for achieving or "setting" instrument accuracy, namely by adjusting the instrument to duplicate a single assay value of a calibrator, such as fresh whole blood, values of which were assigned by a reference method.

Commercial control, while satisfactory, presents a problem of formulation which can make a substantial difference in control stability and performance. The impact of this problem, to a large degree, can be lessened by matching the controls to the instruments and utilizing compatible reagents.

XB analysis is a statistical technique utilizing patient results for continually monitoring COULTER COUNTER analyzers and other apparatus. As conceived by Dr. Brian Bull of Loma Linda University, the XB algorithm is based on the demonstrated stability of the erythrocyte (red cell) indices, mean corpuscular volume (MCV), mean corpuscular hemoglobin (MCH), and mean corpuscular hemoglobin concentration (MCHC) of select patient populations.

Daily instruments checks monitor calibration stability, reproducibility, background counts for confirming the proper functioning of reagent level, diluting and dispensing systems, and general instrument performance.

Interlaboratory comparison programs objectively establish the quality of a laboratory's performance referenced to peer performance for maintaining high performance levels in accordance with the various accreditation criteria of many state, regulatory, and professional agencies.

While each of the above techniques are satisfactory and have permitted achieving a hematologically acceptable degree of control over the accuracy of analytical apparatus, thereby obtaining accurate information about a blood sample, each does suffer from some inherent disadvantages as follows: Whole blood calibration is time consuming. It requires a large quantity of fresh whole blood. As pointed out by Gilmer and Williams in "The Status of Methods of Calibration in Hematology", Am. J. Clin. Path. 74(4): 600, "there is always the real possibility that the mean value obtained may not be accurate". Commercial controls can lead to serious analytical errors through improper use, in storage and handling. Furthermore, there are many circumstances where controls are not practical. XB analysis is not applicable when patient populations are non-representative so as to generate outlying indices, i.e. neonates and oncology patients. Furthermore, XB only monitors ability of original calibration, which could be in error. Also, other generally measured parameters, such as with white cells or platelets, are not monitored by the XB analysis. Professional interlaboratory comparison programs often lead to erroneous interpretation because of specimen/instrument incompatability. The use of a technologist review is at best arbitrary and depends on the skill level of the technologist.

2. Description of the Prior Art

Statistical quality control systems, which aim at determining the statistical distribution of certain quality characteristics of a sample, are disclosed in U.S. Pat. No. 3,151,237. Other types of statistical systems are disclosed in U.S. Pat. No. 4,320,463, in "Medical Research" by John M. England in Chapter 1 thereof, and in "Statistics in Medicine" by Theodore Colton, Sc.D. published by Little, Brown and Company, Boston, Eight Printing (QA-276-Co-1974).

SUMMARY OF THE INVENTION

This invention is an improved procedure for evaluating the accuracy and/or precision of the performance of at least one apparatus in a pool of like apparatuses with respect to the arithmetic mean accuracy and/or precision of the performance of all the apparatuses in the pool. The apparatuses discussed in the preferred embodiment are hematology analyzing apparatuses, although other medical and biological apparatus can well benefit from the invention.

The novel procedure of this invention involves quantitatively analyzing a reference or cell control specimen of known constituents by each apparatus in the pool and collecting the resultant data from the one apparatus in the pool and the arithmetic mean data of the pool apparatus. The data of the one apparatus and of the pool apparatuses are correlated mathematically in a series of statistical equations for computing a novel, sensitive index herein named the "Instrument Performance Index" or IPI. This IPI constitutes a major feature of this invention. This IPI preferably is displayed as a single point in a Cartesian graph, although other graphical and displaying forms of indicia are within the scope of this invention.

This IPI permits an operator of the one apparatus to determine readily the degree of accuracy and/or precision, or conversely the inaccuracy and/or imprecision, of the one apparatus as compared to the accuracy and/or precision of the pool apparatuses. If the IPI indicates an inaccuracy and/or imprecision, the laboratory can consider directly making necessary adjustments or corrections to their apparatus, its environmental conditions, the laboratory routine, the handling and condition of the blood cell control material, etc., for again achieving optimum accuracy and/or precision of the one apparatus. Or, the laboratory can call upon the skill of the customer service department of the manufacturer who, guided by the IQAP and the IPI for each measured parameter, can direct and/or implement the necessary corrections and adjustments.

The reference control or cell sample analyzed by the apparatuses in performance of this invention is preferably whole blood. Other control sample materials can be employed, for example those which contain modified blood components, or components for simulating fresh whole blood, as disclosed in U.S. Pat. Nos. 4,299,726 and 4,405,719 assigned to Coulter Electronics, Inc. Commercially available hematology instrument controls useful in practicing this IQAP invention are 4C ® and 4C ® Plus cell controls produced by the Diagnostics Division of Coulter Electronics, Inc.

This invention is not limited to hematology analyzers of the COULTER COUNTER type, but can be successfully implemented for use with a wide range of apparatuses that would benefit from interlaboratory quality assurance programming.

OBJECTS OF THE INVENTION

The primary object of the invention is to improve upon the prior art interlaboratory quality assurance programs (IQAP) to enable a more readily perceived evaluation of apparatus accuracy and precision.

Another object of the invention is to improve upon IQAP by devising a novel Instrument Performance Index (IPI), which is expressed as a single indicia.

Another object of the invention is formulating a novel Coefficient of Variation Index (CVI), for use with the Standard Deviation Index (SDI), for obtaining the necessary values (coordinates) for defining the IPI, which is representative of the accuracy and precision of an analytical system.

Another object of the invention is the formulation of the novel CVI, which alone defines the precision of an analytical system.

Yet another object of the invention resides in a novel IQAP graphical representation, which readily permits an operator of an analytical procedure and/or apparatus to recognize the need for and possibly even make the required corrections to the procedure and/or apparatus, for achieving the desired precision and accuracy.

Still other objects of the invention will become readily apparent to those skilled in the art in light of the following detailed description of the invention.

BRIEF DESCRIPTION OF THE DRAWINGS

FIGS. 1A–1C illustrate conventional characteristics of accuracy and precision; FIGS. 2A–2D illustrate conventional characteristic distribution patterns that differentiate shifts from trends;

FIG. 3 illustrates a conventional curve of normal distribution showing a comparison of the standard deviation values of a normal distribution; and FIG. 4 illustrates a portion of a novel multiparameter hematology IQAP report form, displaying the novel Instrument Performance Index (IPI) results as one point on each plot.

DETAILED DESCRIPTION OF THE INVENTION

Figure 5:
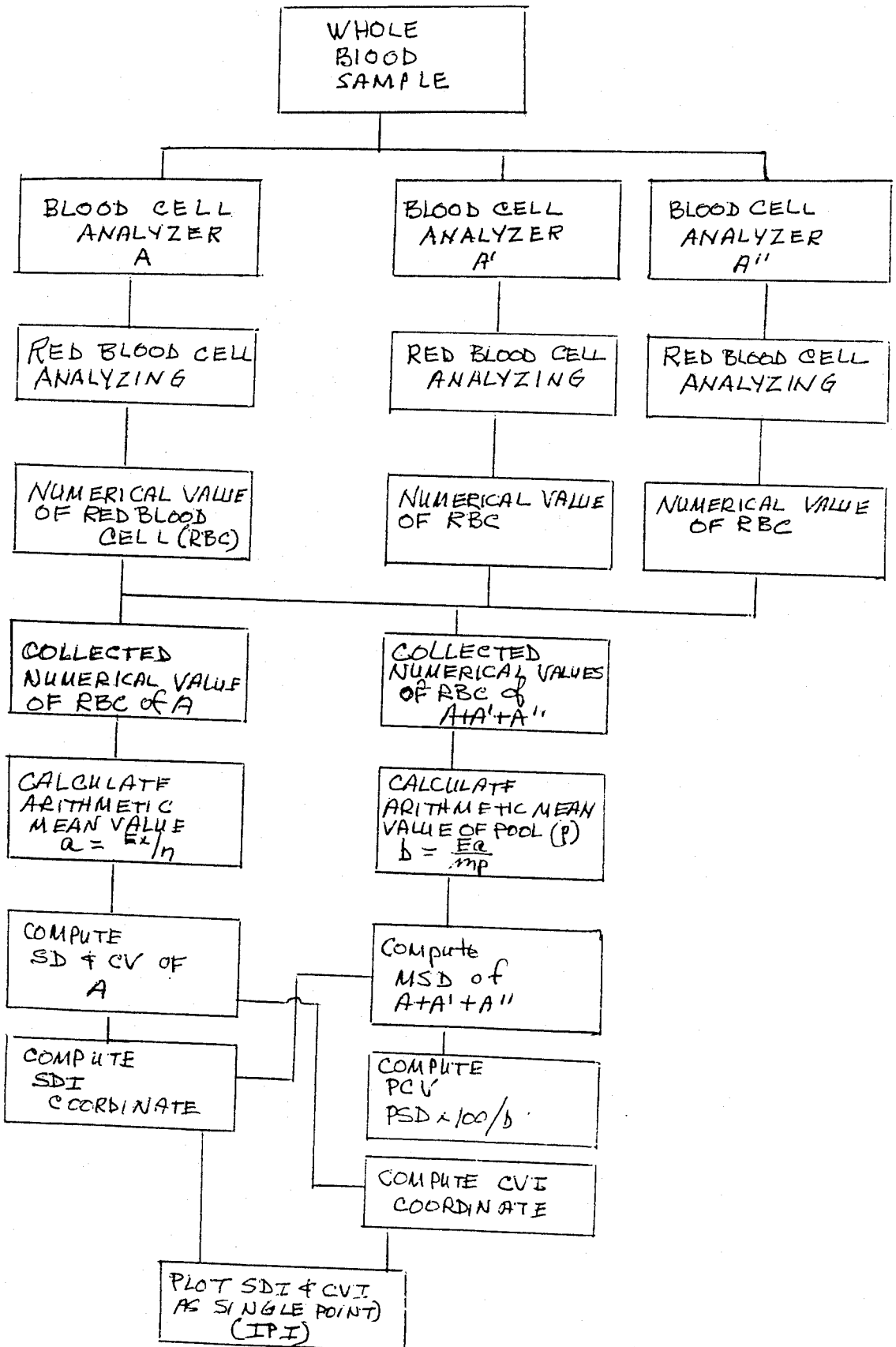
FIG. 5 shows a flow chart in accordance with the present invention.

This invention is an improved procedure for interlaboratory quality assurance (IQAP) for evaluating the accuracy and/or precision of one apparatus in a pool of like apparatuses. Accuracy and precision are terms describing two performance characteristics that determine analytical quality. Accuracy describes the closeness of a measured value to the true or accepted value. Precision describes the closeness of successive measurement of the same value to each other, i.e. reproducibility. The targets illustrated in FIGS. 1A–1C illustrate the characteristics of accuracy and precision. The different arrow locations in the target of FIG. 1A represent poor precision, although one arrow is in the bullseye. The arrows in FIG. 1B are in exactly the same location, thereby representing high precision, but also exemplifying inaccurate performance. FIG. 1C shows a precision and accuracy indicative of especially good performance, since all the arrows are in the bullseye. It is therefore readily apparent that accuracy and precision are separate and distinct functions; however, this invention correlates both accuracy and precision and presents such as a single indicia (IPI); in contrast to prior art IQAP techniques and resulting data formats.

Shifts and trends are known terms describing successive mean-value distribution patterns that indicate developing changes. A shift describes the distribution of six or more successive values, either above or below the target mean. A trend describes the distribution of six or more successive values in one direction, either up or down. A trend can begin above or below the target mean and cross the mean as it develops. FIGS. 2A and 2B show, between dashed lines, an upward and a downward shift, respectively; these shifts having relatively flat distribution patterns compared with the upward and downward trend patterns of FIGS. 2C and 2D. Shifts can be caused by changes in calibration, the concentration of reagents, or the control or assay sample. Trends can be attributed to gradual changes in the reagent or the instrument. This invention can indicate both shifts and trends types of imprecision with a single data indicia, e.g. the Instrument Performance Index point (IPI).

Inasmuch as our invention is a novel procedure which employs statistical formulas from which the quantitative analytical data from one instrument is compared with like data from a pool of like instruments, to obtain our novel Coefficient of Variation Index (CVI) and our novel Instrument Performance Index (IPI), the statistical formulas should be set forth herein, even though most of them are well known.

MATHEMATICAL FORMULAS FOR CALCULATING INDICES

1. Mean Value (a)

The calculation for each laboratory instrument mean value (a) is:

$$a = \frac{Ex}{n}$$

wherein (a) is the mean of the analytical data values derived from the tests (x) from each laboratory instrument, using the same control sample; (E) (representative of the Greek letter Sigma) means the sum of; and (n) is the number of tests. The symbol (a) sometimes is referred to as "X bar".

Mean values are used to statistically measure accuracy against the "known" measurements, i.e. control values. Mean values should be calculated using not less than 16 replicate samples for assuring statistical significance. An n of 16 reduces the error of the mean to less than one standard deviation (SD). The formula of the standard error of the mean (SEM) is:

$$SEM = \frac{a}{\sqrt{n}}$$

2. Pool Mean (b)

The calculation for the pool mean (b) is:

$$b = \frac{Ea}{np}$$

wherein the pool mean (b) is the average of the arithmetic mean values (a) generated by all of the laboratories, including yours; and (np) is the number of reporting laboratories in the pool. The term "peer group" often is employed as meaning pool.

3. Standard Deviation (SD)

The calculation for the standard deviation (SD) is:

$$SD = \sqrt{\frac{Ex^2 - (Ex)^2/n}{n - 1}}$$

wherein (E), (x), (a) and (n) are defined herein above.

Standard deviation (SD) is a measure of the spread of values about a mean value. In quality control (QC), the standard deviation is used to measure precision and generally is expressed in terms of the units used to measure the mean. Precision of your system is evaluated by comparing its standard deviation to the standard deviation values of a pool, as represented by the typical normal distribution curve FIG. 3, where 68% of all the values will fall within ±1.0 measurement unit (1 SD) of the mean, and 95% of all values will fall within ±2 measurement units of the mean (2 SD). In QC, standard deviation values within ±2 SD range denote an acceptable result and standard devaition values within ±1 SD range indicate an even higher degree of accuracy.

4. SD of the Mean (MSD)

The formula for calculating the MSD is:

$$MSD = \sqrt{\frac{Ea^2 - (Ea)^2/L}{L - 1}}$$

wherein the symbols (E), and (a) are defined above and (L) represents the number of laboratory instruments.

SD of the pool mean is the SD calculated from the average of all laboratories' mean values (MSD) and represents the spread of individual means about the pool mean. The MSD is used as the SD value in the calculation of the Standard Deviation Index (SDI) in calculation No. 8 below.

5. Pool SD (PSD)

The formula for calculating the PSD is:

$$PSD = \sqrt{\frac{E[E(x-a)^2]}{n - L}}$$

wherein (E), (L), (x), (a) and (n) are as defined above. The PSD is the weighted average of all laboratories' SD values. It represents the average precision of all laboratories and is used in the calculation of Pool Coefficient of Variation (PCV) in calculation No. 7 below.

6. Coefficient of Variation (CV)

The formula for calculating the CV is:

$$CV = \frac{SD \times 100}{a}$$

wherein (a) and (SD) are as defined above. The coefficient of variation is the standard deviation value expressed as a percentage of the mean value. The system CV, as calculated above, is an integral part of this invention. The comparison of an individual system CV to the pool CV is an index of the system imprecision as defined in calculation No. 9 below.

7. Pool Coefficient of Variation (PCV)

The formula for calculating the PCV is:

$$PCV = \frac{PSD \times 100}{b}$$

The PCV is the PSD expressed as a percentage of the pool mean (b). It represents pool precision and is used in the calculation of system imprecision in calculation 9 below. In general terms, the PCV states the averge imprecision of the pool against which your system imprecision is measured.

8. Standard Deviation Index (SDI)

The formula for calculating the SDI is:

$$SDI = \frac{a - b}{MSD}$$

The Standard Deviation Index is a comparative measure of the closeness of your mean value to the pool mean. This invention utilizes the SDI value as an index of system accuracy relative to the pool mean. An SDI of greater than ±2 identifies individual system inaccuracy.

9. Coefficient of Variation Index (CVI)

The formula for calculating the CVI is:

$$CVI = \frac{CV}{PCV}$$

The coefficient of Variation Index is a novel comparative measure of your system imprecision relative to that of the pool imprecision. This invention utilizes this CVI measurement to identify systems with poor precision when referenced to the pool precision.

The thus obtained Standard Deviation Index (SDI) and new Coefficient of Variation Index (CVI) are combined by our invention to constitute the set of coordinates in the Cartesian coordinate system of a graph. This set is plotted as a dot on a graph as illustrated in FIG. 4. This focal point constitutes the novel Instrument Performance Index (IPI) of our invention. The location of the IPI visually indicates the precision and accuracy of the instrument or apparatus resulting from the performance of one apparatus as compared to the precision and accuracy of the pool of like apparatuses. This Instrument Performance Index (IPI) is a novel and unexpected derived indicia, more specifically, a dot or a point, that denotes the combined influence of previously independent system performance indicators.

As discussed hereinabove, this invention can provide an improvement in IQAP for hematology analyzers which measure several blood parameters. Each analyzer (generic term being apparatus) in the peer group pool, is of the same type and utilizes the same test sample or specimen, examples of which are 4C ® and 4C ® Plus cell control. To be the "same" test sample would mean that such a cell control is from the same manufacturing lot, so that the multiparameter blood constituents therein are identical for all apparatus in the pool. Likewise, our invention advantageously can be employed in an IQAP for chemical analyzers, one example being the COULTER ® DACOS ® chemistry system, which can analyze for numerous different analytes; and control solutions exist which can act as the sample material.

The resulting plotting of the Instrument Performance Index (IPI) point on each of several graphs is shown in FIG. 4, with respect to seven different blood parameters, as can be measured by a COULTER COUNTER Model S type analyzer, using as the test or specimen material 4C or 4C Plus cell control lot number 443; the participating laboratory being PRH 205. Portions of the individual graphs can be color keyed, shaded, or otherwise differentiated to enhance the visual recognition of desirable and undesirable IPI indicia positions. The desirable/acceptable performance limits shown in FIG. 4 lie within a rectangle defined by ±2 SDI along the baseline and 2 CVI, which is differently "framed" from the areas exterior of such rectangle on the graph. The closer the IPI dot is to the "MEAN" line which is midway between +1 SDI and −1 SDI, the greater is the accuracy of the instrument. The closer the dot is to the baseline, the greater is the precision. In coordinate system technology, a middle or mean distance along the ordinate or X-axis designates best accuracy; whereas, a zero value for the abscissa or CVI is optimal. Hence, the closer that the IPI single indicia is to both the MEAN line and the baseline, the better is the system performance with respect to both accuracy and precision, respectively.

In the WBC plot of FIG. 4, the IPI dot exactly is centered on the MEAN line and is extremely close to the baseline. Hence, this IPI plot represents a near perfect performance, both accurate (SDI) and precise (CVI) relative to the pool data. The RBC graph in FIG. 4 shows the single indicia centered on the mean line, but at a height of 2.5 CVI. Here the performance is highly accurate (SDI), but compared with the pool of like apparatuses (CVI to baseline), it is imprecise. The Hgb plot shows the dot close to the CVI baseline, but located at −2.5 SDI. This illustrates good precision, but unacceptable accuracy. The performance of the PRH 205 instrument with respect to Hct is both poor in accuracy and poor in precision, since the IPI dot is located too high on the rectangular plot and too far from the MEAN line. As easily seen, the IPI indicia in all three plots RBC, Hgb and Hct lie outside of the acceptable performance rectangle. The IPI resultant for each of MCV, PLT, and MPV is within acceptable precision and accuracy limits as defined by the pool data, with the MPV correlation being the best of these three.

The interpretative value of these performance matrix plots is immense. One can tell at a glance the relative accuracy and precision of his instrument, or conversely its inaccuracy and imprecision, compared to all other participants in the pool.

Notwithstanding the significant improvement our IPI provides to IQAP when the SDI and CVI values are a single point on a Cartesian coordinate system, the SDI and CVI values themselves are an improvement over the prior art IQAP and can be presented as a pair or set of values for operator consideration. This set of SDI and CVI values can be listed on a table of resultant values, as will be expained with respect to Table III herein below.

Additionally, the novel Coefficient of Variation Index (CVI), by itself, provides precision information not previously available and it can be derived easily, without need of calculations 4 and 8 for display, printout, etc.

The data needed from each instrument of the peer group pool can be obtained by various means, depending upon the sophistication of the instruments and the IQAP processing center. Fully automatic data transfer by telemetry or remote data acquisition, semi-automatic data transfer by telephone-modem or facsimile equipment, and primarily manual data transfer all are within the skill of the art. Next will be described, with reference to Tables I and II, a primarily manual mode of data communication from the laboratories to the IQAP processing center, followed by the data handling and resultant development at the processing center, and then transmittal of the IQAP report to each laboratory.

To facilitate raw data transmittal from each IQAP laboratory, there can be a simple data entry form, the top portion of an example of which is shown partially completed in Table I. Depending upon the apparatus, the identity of the test parameters can be in columns, with the individual entries, for example one each day of the month, manually listed therebelow. A daily entry for approximately one month can provide statistically sufficient data. It is to be remembered that all numbers of the IQAP pool will be using the "same" test sample for the same reporting period. At the end of the reporting period, the data entry form would be mailed from each pool laboratory to the IQAP processing center. The IQAP processing center then would compile all of the data, perform the computations to obtain the CVI, SDI and IPI, preferably generate the IPI plots shown in FIG. 4, as well as the data of Table II discussed below and, where needed, give guidance to each laboratory for improving the precision and accuracy of its apparatus and its system. The term "system" is used herein to include variables beyond that of the apparatus per se and includes laboratory operations which can influence the performance of the apparatus.

Table II presents the individual and comparative IQAP statistics and the ultimately derived values for SDI and CVI. The term "YOUR" designates the one apparatus being compared to all of the apparatuses in the pool. From left to right, the first columns of Table II list: each tested parameter, the assay values of the sample or specimen material, the mean (a) for your apparatus, and the mean (b) for the pool apparatuses. The next three columns list the Standard Deviations: for your apparatus (SD), the pool (PSD), and the Standard Deviation of the Mean (MSD). The next four columns depict the Coefficient of Variation (CV) for your apparatus for the present reporting period and the two previous reporting periods, and that of the pool apparatuses (PCV). Next listed in Table II is the number of laboratories (LABS) including your laboratory and the number of test values (n) included in the calculations. The last two columns present the Standard Deviation Index (SDI) and Coefficient of Variation Index (CVI), respectively.

The data presented in Table I, Table II and the IPI indicia of FIG. 4 are not based upon a common set of information, nor derived from one another. However, Table II raw data was obtained from a peer group of hematology instruments and the derived data in Table II was developed from such raw data by use of the procedure of this invention.

Now with reference to the top row of information in Table II, which concerns the white blood cell count (WBC) parameter, and reading from left to right, the assay value 7.4 provides a reference for the reader of Table II in considering the adjacent values of the mean of his apparatus and the pool apparatuses. However, this assay value is not utilized as part of the data base of the statistics for the procedure of our invention. In this example, the mean value (a) of your instrument is 7.8 and pool mean (b) is 7.28, which when compared to the assay value of 7.4 would indicate that your mean value not only is further from the assay value than is the pool value, but also that your mean value is greater than the assay value; whereas, the pool mean value is less than the assay value. Hence, your WBC data initially is suspect. Your SD is 0.11, the PSD is 0.15, and the MSD is 0.12. This set of data would indicate that, with respect to Standard Deviation, the operation of your instrument is better than that of the pool. Your CV is 1.41, that of the pool is 2.00, and your previous two months were 1.76 and 2.15, respectively. Inspection of this set of data shows that your WBC parameter CV is acceptable and has improved in each of the recent three months. The number of laboratories (L) 300 and your tests (n) 28 indicates that your data, the pool data, and therefore the derived data for the WBC analysis are statistically sound.

Your SDI of 2.50 and CVI of 0.71 show that your system performance, with respect to WBC test analysis, is not acceptable, because it is inaccurate, having a high SDI of 2.50, even though your system performance is precise with a small CVI of 0.71. If these SDI and CVI values had been plotted as the IPI point for WBC in FIG. 4, that IPI point would have been near the middle of the lowest right end part of box and outside of the acceptable "framed" area.

A similar analysis of the RBC values in the second row of Table II would indicate favorable data, resulting in a SDI of −0.88 and a CVI of 0.84, both of which are very acceptable and would result in an IPI plot point lying in the box which is in the lowest row and just to the left of the MEAN line; ie, an indication of high precision and high accuracy and lying well inside the "framed" portion.

Hence, a simple listing of the SDI and CVI values, as in Table II, can be interpreted relatively easily to advise a laboratory of the accuracy and precision, respectively, of its instrument and system for each tested parameter, without need for the ultimate physical plotting of the IPI point. Therefore, this invention permits a subscriber of our improved IQAP to ascertain quickly by visual observation of the single IPI indicia and/or its SDI and CVI components the accuracy and precision of a particular analytical apparatus, instrument and system in comparison to the identical or substantially identical pool of such apparatuses and instruments, with respect to each separate test parameter. Additionally, our novel CVI value itself provides precision information and the SDI value provides accuracy information.

Although there has been disclosed an embodiment directed to blood analyzing apparatus and hematology parameters, it now should be readily apparent that the disclosed invention readily is applicable for determining the accuracy and/or precision of other types of analyzers, for example, colorimeters, chromatography apparatus, etc. Now therefore, variations, of our invention lie within the reach and capability of those skilled in the art without departing from the scope and spirit of the invention as next claimed.

TABLE I

| | IQAP DATA ENTRY FORM | | | | | |
| | LAB I.D.: PRH 205 | | | LOT NO.: 443 | | |
| DATE | WBC | RBC | Hgb | Hct | MCV | MCH | MCHC |
|---|---|---|---|---|---|---|---|
| 11-1 | 8.3 | 4.26 | 12.2 | 36.3 | 87.0 | | |
| 11-2 | 8.2 | 4.22 | 12.1 | 36.4 | 88.0 | | |
| 11-4 | 8.0 | 4.26 | 12.0 | 36.6 | 87.0 | | |
| 11-5 | 8.2 | 4.24 | 12.1 | 36.5 | 88.0 | | |

TABLE II

| | INTERLABORATORY QUALITY ASSURANCE PROGRAM | | | | | | | | | | | | | |
| | | Prepared for: MEAN | | SD | | | CV | | | | | | | |
| | ASSAY | YOUR | POOL | YOUR | POOL | MEAN | YOUR | 1 | 2 | POOL | LABS | N. | SDI | CVI |
|---|---|---|---|---|---|---|---|---|---|---|---|---|---|---|
| WBC | 7.4 | 7.8 | 7.28 | .11 | .15 | .12 | 1.41 | 1.76 | 2.15 | 2.00 | 300 | 28 | 2.50 | .71 |
| RBC | 4.28 | 4.25 | 4.28 | .035 | .042 | .034 | .82 | .91 | .35 | .98 | 300 | 28 | −.88 | .84 |
| Hgb | 12.6 | 12.7 | 12.6 | .07 | .12 | .11 | .55 | .84 | .71 | .95 | 300 | 28 | .91 | .58 |
| Hct | 36.3 | 36.2 | 36.2 | .30 | .38 | .36 | .83 | .84 | .73 | 1.05 | 300 | 28 | .00 | .79 |
| MCV | 84.7 | 85.1 | 84.6 | .35 | .48 | .57 | .41 | .64 | .70 | .57 | 300 | 28 | .88 | .72 |
| MCH | 29.4 | 30.0 | 29.5 | .24 | .36 | .31 | .80 | 1.31 | .72 | 1.22 | 300 | 28 | 1.61 | .66 |
| MCHC | 34.7 | 35.3 | 34.9 | .28 | .44 | .40 | .79 | 1.08 | .85 | 1.26 | 299 | 28 | 1.00 | .63 |

What we claim is:

1. A procedure for evaluating statistically the performance of at least one apparatus in a pool of like apparatuses, by comparing the performance of said one apparatus with the performance of said like apparatuses, and by providing at least one comparative performance indicator of said one apparatus, said procedure comprising the steps of:
- performing at least one substantially identical operation by each of said apparatuses in said pool;
- producing, as a result of said performing operation, associated resultant data by each of said apparatuses, for each separate operation;
- collecting said resultant data from said one apparatus and said like apparatuses;
- calculating from said resultant data the arithmetic mean data of all of the pool apparatuses;
- translating mathematically said resultant data from said one apparatus and said arithmetic mean data from said pool apparatuses into at least one performance value for each said operation; and
- providing said performance value as an indicator specific to the precision of performance of said one apparatus as compared to the precision of performance of the pool apparatuses.

2. A procedure for evaluating statistically the performance of at least one apparatus in a pool of like apparatuses, by comparing the performance of said one apparatus with the performance of said like apparatuses, and by providing comparative performance indicators of said one apparatus, said procedure comprising the steps of:
- performing at least one substantially identical operation by each of said apparatuses in said pool, said operation including analyzing quantitatively a reference specimen having at least one known constituent;
- producing, as a result of said performing operation, associated resultant data by each of said apparatuses, for each separate operation;
- collecting said resultant data from said one apparatus and said like apparatuses;
- calculating from said resultant data the arithmetic mean data of all of the pool apparatuses;
- translating mathematically said resultant data from said one apparatus and said arithmetic mean data from said pool apparatuses into one pair of performance values for each said operation, said pair of performance values being indicators respectively specific to the accuracy and precision of performance of said one apparatus as compared to the accuracy and precision of performance of the pool apparatuses; and
- displaying graphically said pair of performance values as a single point, by using them as a pair of coordinates in a Cartesian coordinate system, said single point indicating both said accuracy and precision.

3. A procedure for evaluating statistically the performance of at least one apparatus in a pool of like apparatuses, by comparing the performance of said one apparatus with the performance of said like apparatuses, and by providing at least one comparative performance indicator of said one apparatus, said procedure comprising the steps of:
- performing at least one substantially identical operation by each of said apparatuses in said pool;
- producing, as a result of said performing operation, associated resultant data by each of said apparatuses, for each separate operation;
- collecting said resultant data from said one apparatus and said like apparatuses;
- calculating from said resultant data the arithmetic mean data of all of the pool apparatuses;
- computing mathematically from said resultant data and said arithmetic mean data the standard deviation and the coefficient of variation for said one apparatus and said pool apparatuses, and
- deriving therefrom at least one of (a) a Coefficient of Variation Index performance value and (b) a Coefficient of Deviation Index performance value, and
- providing said performance value as an indicator specific to at least one of (a) the precision of and (b) the accuracy of performance of said one apparatus as compared to at least one of said precision and said accuracy of performance of the pool apparatuses.

4. A procedure according to claim 3, wherein said deriving of said Coefficient of Variation Index is from the formula $$CVI = \frac{CV}{PCV};$$

wherein CV is the coefficient of variation, as exemplified by the formula 6 of the Specification, and PCV is the pool coefficient of variation, as exemplified by formula 7 of the Specification; said formulas being:

6. Coefficient of Variation $CV = SD \times 100/a$;
7. Pool Coefficient of Variation $PCV = PSD \times 100/b$; and
PSD is the pool standard deviation,
a is mean value, and
b is pool mean.

5. A procedure according to claim 3, wherein said Coefficient of Variation Index is as defined by formula 9 of the Specification, and said computing includes mathematically calculating such precision index in accordance with formulas 1, 2, 5, 6, and 7 of the Specification; said formulas being:

1. Mean Value $a = Ex/n$;
2. Pool Mean $b = Ea/np$;
5. Pool SD PSD $$= \sqrt{\frac{E[E(x-a)^2]}{n-L}};$$

6. Coefficient of Variation $$CV = \frac{SD \times 100}{a};$$

7. Pool Coefficient of Variation PCV $$= \frac{PSD \times 100}{b}; \text{ and}$$

9. Coefficient of Variation Index $$CVI = \frac{CV}{PCV};$$

and

E (representative of the Greek letter Sigma) means the sum of, x is the data values derived from the tests or operations from each apparatus in the pool, n is the number of tests, and np and L are the number of apparatuses in the pool.

6. A procedure according to claim 3, wherein said Coeffecient of Deviation Index is defined by formula 8 of the Specification, and said computing includes mathematically calculating in accordance with formulas 1, 2, and 4 of the Specification; said formulas being:

1. Mean Value $a = Ex/n$;
2. Pool Mean $b = Ea/np$;
4. SD of the Mean $$MSD = \sqrt{\frac{Ea^2 - (Ea)^2/L}{L-1}} \ ;$$

and

8. Standard Deviation Index $SDI = a - b/MSD$; and

E (representative of the Greek letter Sigma) means the sum of, x is the data values derived from the tests or operations from each apparatus in the pool, n is the number of tests, and np and L are the number of apparatuses in the pool.

7. A procedure according to claim 3 wherein said Coefficient of Variation Index and said Coefficient of Deviation Index by said step of deriving, provids a pair of values which define coordinates, and said procedure further comprises displaying said coordinates for visual interpretation.

8. A procedure to claim 3, wherein said performing of said operation by said pool apparatuses includes analyzing a reference specimen having at least one known constituent.

9. A procedure according to claim 8, wherein said reference specimen is a whole blood cell control, and said apparatuses are blood cell analzyers.

10. A procedure for evaluating statistically the performance of at least one apparatus in a pool of like apparatuses, by comparing the performance of said one apparatus with the performance of said like apparatuses, and by providing at least one comparative performance indicator of said one apparatus, said procedure comprising the steps of:

performing at least one substantially identical operation by each of said apparatuses in said pool;

producing, as a result of said performing operation, associated resultant data by each of said apparatuses, for each separate operation;

collecting said resultant data from said one apparatus and said like apparatuses;

calculating from said resultant data the arithmetic mean data of all of the pool apparatuses;

translating mathematically said resultant data from said one apparatus and said arithmetic mean data from said pool apparatus into a pair of performance values which define coordinates, one specific to precision and the other specific to accuracy as compared to the precision and accuracy of the pool apparatuses; and displaying said pair of coordinates as a single point for visual interpretation, said single point indicating both the accuracy and precision.

11. A procedure according to claim 10, in which said displaying further includes the step of displaying graphically said single point in a Cartesian coordinate system.

12. a procedure according to claim 10, wherein said single point defines an Instrument Performance Index.

13. A procedure according to claim 10, whrein said displaying includes formatting the Cartesian coordinate system to define an area of acceptable values for said single point.

14. A procedure for evaluating statistically the performance of at least one apparatus in a pool of like apparatuses, by comparing the performance of said one apparatus with the performance of said like apparatuses, and by providing at least one comparative performance indicator of said one apparatus, said procedure comprising the steps of:

performing at least one substantially identical operation by each of said apparatuses in said pool;

producing, as a result of said performing operation, associated resultant data by each of said apparatuses, for each separate operation;

collecting said resultant data from said one apparatus and said like apparatuses;

calculating from said resultant data the arithmetic mean data of all of the pool apparatuses;

translating mathematically said resultant data from said one apparatus and said arithmetic mean data from said pool apparatus into a pair of performance values for each said operation, one specific to precision and the other specific to accuracy, both specific to said one apparatus as compared to the precision and accuracy of the pool apparatuses, said precision performance value being defined as the Coefficient of Variation Index, and said accuracy performance value as the Standard Deviation Index.

15. A procedure according to claim 14, wherein said Standard Deviation Index is defined by formula 8 of the Specification, and Coefficient of Variation Index is defined by formula 9 of the Specification; said formulas being:

8. Standard Deviation Index $SDI = a - b/MSD$; and
9. Coefficient of Variation Index $CVI = CV/PCV$; and a is the mean value, b is pool mean, MSD is Standard Deviation of the Mean, CV is the Coefficient of Variation, and PCV is the Pool Coefficient of Variation.

* * * * *